US006929794B1

(12) United States Patent
Mills et al.

(10) Patent No.: US 6,929,794 B1
(45) Date of Patent: Aug. 16, 2005

(54) **IL-12 AS AN ADJUVANT FOR *BORDETELLA PERTUSSIS* VACCINES**

(75) Inventors: Kingston H. G. Mills, Co. Kildare (IE); Bernard P. Mahon, Co. Kildare (IE); Mark S. Ryan, Co. Kildare (IE); Fiona Griffin, Co. Kildare (IE)

(73) Assignee: National University of Ireland, Maynooth (IE)

( * ) Notice: Subject to any disclaimer, the term of this patent is extended or adjusted under 35 U.S.C. 154(b) by 0 days.

(21) Appl. No.: 09/182,824

(22) Filed: Oct. 29, 1998

Related U.S. Application Data

(63) Continuation of application No. 08/829,865, filed on Mar. 31, 1997, now abandoned.
(60) Provisional application No. 60/015,871, filed on May 31, 1996.

(51) Int. Cl.[7] ........................ A61K 39/00; A61K 39/02; A61K 39/10; A61K 45/00
(52) U.S. Cl. ................................ 424/184.1; 424/234.1; 424/253.1; 424/254.1; 424/278.1
(58) Field of Search ........................... 424/184.1, 234.1, 424/253.1, 254.1, 278.1

(56) References Cited

U.S. PATENT DOCUMENTS

| | | | | |
|---|---|---|---|---|
| 4,518,584 A | | 5/1985 | Mark et al. | |
| 4,705,686 A | * | 11/1987 | Scott et al. | |
| 5,427,788 A | * | 6/1995 | Rappuoli et al. | 424/190.1 |
| 5,444,159 A | * | 8/1995 | Jackson et al. | 530/412 |
| 5,571,515 A | | 11/1996 | Scott et al. | |
| 5,723,127 A | * | 3/1998 | Scott et al. | 424/184.1 |

FOREIGN PATENT DOCUMENTS

| | | |
|---|---|---|
| EP | 0 441 900 B1 | 8/1991 |
| JP | 01 193231 | 8/1989 |
| WO | WO 90/05147 | 5/1990 |
| WO | WO 91/01143 | 2/1991 |
| WO | WO 94/01139 | 1/1994 |
| WO | WO 96/01272 | 1/1996 |
| WO | WO 96/10423 | 4/1996 |
| WO | WO 96/11019 | 4/1996 |
| WO | WO 96/40267 | 12/1996 |
| WO | WO 97/00321 | 1/1997 |

OTHER PUBLICATIONS

Markoff et al. Bio/Technology 8: 1030–1033, 1990.*
Petersen et al. Vaccine 11(4):463–472, 1993.*
Redhead et al (Infection & Immunity vol. 61, No. 8. pp 3190–3198), Aug. 1993.*
Scott P., "IL–12 Initiation Cytokine for Cell–Mediated Immunity" *Science*, 260:496–497 (1993).
McDowell R. S. et al., J Amer Chem Soc 114:9245–9253 (1992).
Cohen J., Science 259:1691–1692 (1993).
Fynan E. et al., PNAS USA 90:11478–11482 (1993).
Wolff J. A. et al., Biotechniques 11:474–485 (1991).
Mahon B. P. et al., J Exp Med 181:1285–1292 (1995).
Sato et al., Infect Immun 29:261–266 (1980).
Ryan et al., Immunology 83 Supp 1:34 Abstract 5.7 (1994).
Mills, K. G. H., NIH Meeting Abstract (1996).
Ad Hoc Group for the Study of Pertussis Vaccines, Lancet 1 (8592): 955–60 (1988).
Afonso et al., Science 263: 235–237 (1994).
Bannatyne and Jackowski, Vaccine 5: 268–269 (1987).
Greco et al., N Engl J Med 334(6): 341–348 (1996).
Gustafsson et al., N Engl J Med 334(6): 349–355 (1996).
Miller et al., J Immunol. 115: 4817–4828 (1995).
Ryan et al., Dev Biol Stand 89: 297–305 (1997).
Schijns et al., J. Immunol 155: 2525–2532 (1995).
Sidey et al., Vaccine 7: 237–241 (1989).
Skeen et al., J Immunol 156: 1196–1206 (1996).
Mahon et al., Infect Immun 64: 5295–5301 (1996).
Bliss J. et al., J Immunol 156:887–894 (1996).
McKnight A. J. et al., J Immunol 152:2172–2179 (1994).
Seder R. A. et al., PNAS USA 90:10188–10192 (1993).
Morris S. C. et al., J Immunol 152:1047–1056 (1994).
Flynn J. L. et al., J Immunol 62:2515–2524 (1995).
Gazzinelli R. T. et al., PNAS USA 90:6115–6119 (1993).
Heinzel F. P. et al., J Exp Med 177:1505–1509 (1993).
Hunter C. A. et al., Infect Immun 62:2818–2824 (1994).
Sypek J. P. et al., J Exp Med 177:1797–1802 (1993).
Tripp C. S. et al., J Immunol 152:1883–1887 (1994).
Urban J. F. et al., J Immunol 156:263–268 (1996).
Wynn T. A. et al., J Exp Med 179:1551–1561 (1994).
Zhan Y. et al., Infect Immun 63:1387–1390 (1995).
Renauld–Mongenie G. et al., PNAS USA 93:7944–7949 (1996).
Steffen P. et al., EMBO J 15:102–109 (1996).
Kobayashi M. et al., J Exp Med 170:827 (1989).
Saragovi H. U. et al., Bio/Technology 10:773–778 (1992).
Hausman S. Z. et al., Infect Immun 64:4020–4026 (1996).
LeBlay K. et al., Microbiology 142:971–978 (1996).
Robinson A. et al., Vaccine 3:11–22 (1985).
Friedman R. L. et al., Infect Immun 60:4578–4585 (1992).
Saukkonen K. et al., J Exp Med 173:1143–1149 (1991).
Mills K. H. G. et al., J Med Microbiol 39:163–164 (1993).
Peppoloni S. et al., Infect Immun 59:3768–3773 (1991).
Peterson J. P. et al., Infect Immun.60:4563–4570 (1992).
Mosmann T. R. et al., Adv Immunol 46:111–147 (1989).
Mills K. H. G. et al., Infect Immun 61:399–410 (1993).
Redhead K. et al., Infect Immun 61:3190–3198 (1993).
Barnard A. et al., Immunol 87:372–380 (1996).
Gajewski T. F. et al., J Immunol 146:1750–1758 (1991).
O'Garra A. et al., Curr Opin Immunol 6:458–466 (1994).
Hsieh C. S. et al., Science 260:547–549 (1993).
Trinchieri G., Annu Rev Immunol 13:251–276 (1995).

* cited by examiner

*Primary Examiner*—Mark Navarro
(74) *Attorney, Agent, or Firm*—Finnegan, Henderson, Farabow, Garrett & Dunner, LLP

(57) ABSTRACT

This invention provides a composition of at least one *Bordetella* antigen and an effective adjuvant amount of interleukin-12 (IL-12), and uses thereof as a vaccine against *Bordetella* infection. Methods for using IL-12 as an adjuvant in combination with vaccines against *Bordetella* are also provided.

43 Claims, 4 Drawing Sheets

IL-12 AS AN ADJUVANT FOR *BORDETELLA PERTUSSIS* VACCINES

This application is a continuation of application Ser. No. 08/829,865, filed Mar. 31, 1997, now abandoned, which claims priority from provisional application 60/015,871, filed 31 May 1996 now abandoned.

BACKGROUND OF THE INVENTION

The present invention relates generally to vaccines against *Bordetella* species that include interleukin-12 (IL-12) as an adjuvant, and to methods for using IL-12 as an adjuvant in or in combination with such vaccines.

Colonization of the respiratory tract by the Gram-negative coccobacillus *Bordetella pertussis* results in whooping cough, also called pertussis, a significant cause of morbidity and mortality of human infants. Two other closely-related isolates of *Bordetella* have also been found in humans: *B. parapertussis* and *B. bronchiseptica*. Molecular genetic analyses suggests that these three isolates are too closely related to be classified as separate species. (Gilchrist, M. J. R., 1991, "*Bordetella*", in *Manual of Clinical Microbiology*, $5^{th}$ ed., Balows, A. et al., American Society for Microbiology, Washington, D.C.) While *B. pertussis* differs from *B. bronchiseptica* and *B. parapertussis* in the nature of the toxins it produces, *B. bronchiseptica* and *B. parapertussis* do produce active toxins (Hausman, S. Z. et al., 1996, *Infect. Immun.* 64: 4020–4026), and there is some evidence to indicate that *B. pertussis* organisms can covert to the *B. parapertussis* phenotype (Gilchrist, M. J. R., 1991, "*Bordetalla*", in *Manual of Clinical Microbiology*, $5^{th}$ ed., Balows, A. et al., eds., American Society for Mircobiology, Washington, D.C.). Although *Bordetalla* isolates exhibit some surface antigens that differ between isolates, monoclonal antibodies that recognize one isolate often recognize at least one other isolate (LeBlay, K. et al., 1996, *Microbiology* 142: 971–978). The high degree of molecular similarity between *Bordetella* isolates and the cross-reactivity of monoclonal antibodies to *Bordetella* antigens indicates that the immune response product by a vaccine against one *Bordetella* isolate would likely affect the other isolates as well.

Immunization with a whole-cell *Bordetella pertussis* vaccine have proved efficacious in controlling pertussis, but concern has been raised over its reactogenicity. Pertussis acellular vaccines are significantly less reactogenic but are of varying efficacy. Until recently the bacterium was thought to occupy a purely extracellular niche during infection and consequently humoral immune mechanisms were assumed to be paramount in protection. (Robinson, A. et al., 1985, *Vaccine* 3: 11–22). However, there is increasing evidence from human and murine studies that *B. pertussis* can also occupy an intracellular niche through invasion and survival within lung macrophages and other cell types. (Friedman, R. L. et al., 1992, *Infect. Immun.* 60: 4578–4585; Saukkonen, K. et al., 1991, *J. Exp. Med.* 173: 1143–1149). These observations have let to a reexamination of the mechanisms of protective immunity against *B. pertussis*. While antibody plays a role in bacterial toxin neutralization and in the prevention of bacterial attachment following transudation of circulating immunoglobulin (Ig) into the lung, cell-mediated immunity also plays a significant role in protection against *B. pertussis* (Mills, K. H. G. and K. Redhead, 1993, *J. Med. Microbiol.* 39: 163–164; Peppoloni, S. et al., 1991, *Infect. Immun.* 59: 3768–3773; Peterson, J. P. et al., 1992, *Infect. Immun.* 60: 4563–4570.)

The current understanding of the role of $CD4^+T$ helper (Th) cells in immunity to infectious diseases is that antigen-specific type 1 T helper (Th1) cells which secrete interferon-γ (IFN-γ), interleukin-2 (IL-2), and tumor necrosis factor-β (TNF-β) mediate cellular immunity, delayed-type hypersensitivity, and inflammatory responses, whereas type 2 T helper (Th2) cells which secrete the interleukins IL-4, IL-5, and IL-6 are considered to be mainly responsible for the provision of specific T cell help for antibody production. (Mosmann, T. R. and R. L. Coffman, 1989, *Adv. Immunol.* 46: 111–147.) Previous studies using a murine respiratory model have demonstrated that protective immunity against *B. Pertussis* induced by infection is mediated by a $CD4^+$ T cell population that secreted IL-2 and IFN-γ (Th1 cells). Adoptive transfer experiments demonstrated that protection could be conferred with T cells in the absence of detectable antibody responses. In a study of vaccine-induced immunity, immunization with the whole-cell pertussis vaccine selectively induced Th1 cells, whereas an acellular vaccine, comprising the *B. pertussis* antigens detoxified PT, FHA, and pertactin, induced Th2 cells. Furthermore, the induction of a Th1 response following infection or immunization with the whole-cell vaccine was associated with earlier bacterial clearance following respiratory challenge. (Mills, K. H. G. et al., 1993, *Infect. Immun.* 61: 399–410; Redhead, K. et al., 1993, *Infect. Immun.* 61: 3190–3198.)

The polarization of $CD4^+$ T cell cytokine production towards type 1 or type 2 responses following in vivo priming appears to be controlled by a number of factors including the nature of the immunogen, the route of immunization, and the antigen-presenting cell and regulatory cytokine milieu at the site of T cell stimulation. (Barnard, A. et al., 1996, *Immunol.* 87: 372–380; Gajewski, T. F. et al., 1991, *J. Immunol.* 146: 1750–1758; O'Gara, A. and K. Murphy, 1994, *Curr. Opin. Immunol.* 6: 458–466.) The regulatory cytokine interleukin-12 (IL-12) is also a key cytokine in the development of type 1 responses. (Hsieh, C.-S. et al., 1993, *Science* 260: 547–549; Trinchieri, G., 1995, *Annu. Rev. Immunol.* 13: 251–276.) IL-12 can induce the secretion of IFN-γ by natural killer (NK) cells and by $CD4^+T$ cells and can promote the differentiation and development of Th1 cells from Th0 precursor populations. (Bliss, J. et al., 1996, *J. Immunol.* 156: 887–894; McKnight, A. J. et al., 1994, *J. Immunol.* 152: 2172–2179; Seder, R. A. et al., 1993, *PNAS USA* 90: 10188–10192.) Furthermore, IL-12 may also induce the production of opsonizing antibodies, by promoting IFN-γ-mediated immunoglobulin (Ig) class switching in favor of IgG2a in the mouse. (Morris, S. C. et al., 1994, *J. Immunol.* 152: 1047–1056.) Since Th1 cells play an important role in the resolution of infections with intracellular organisms, IL-12 can influence the course of bacterial, viral, and parasitic infections by altering the balance of Th1 and Th2 cells in favor of IFN-γ production. (Flynn, J. L. et al., 1995, *J. Immunol.* 155: 2515–2524; Gazzinelli, R. T. et al., 1993, *PNAS USA* 90: 6115–6119; Heinzel, F. P. et al., 1993, *J. Exp. Med.* 177: 1505–1509; Hunter, C. A. et al., 1994, *Infect. Immun.* 62: 2818–2814; Sypek, J. P. et al., 1993, *J. Exp. Med.* 177: 1797–1802; Tripp, C. S. et al., 1994, *J. Immunol.* 152: 1833–1887; Urban, J. F. et al., 1996, *J. Immunol.* 156: 263–268; Wynn, T. A. et al., 1994, *J. Exp. Med.* 179: 1551–1561; Zhan, Y. and C. Cheers, 1995, *Infect. Immun.* 63: 1387–1390.)

There is a continuing requirement for new composition comprising IL-12 that will enhance or alter the effects of *Bordetella* vaccines, and for methods for their use in the prevention, treatment, or amelioration of *Bordetella* infections.

SUMMARY OF THE INVENTION

The present invention is based on the discovery that the use of IL-12 as an adjuvant in an acellular *Bordetella* vaccine significantly increased its protective efficacy.

In one embodiment, the present invention provides a composition comprising at least one *Bordetella* antigen and an effective adjuvant amount of interleukin-12. Preferably, the antigen is a *Bordetella pertussis* antigen, or is lipopolysaccharide, pertussis toxin, filamentous hemagglutinin, or pertactin, or is adsorbed to alum.

In another embodiment, the invention provides a composition comprising an effective adjuvant amount of interleukin-12 and at least one antigen-encoding polynucleotide capable of expression in vivo to produce at least one *Bordetella* antigen.

A further embodiment provides a composition comprising at least one *Bordetella* antigen and an interleukin-12-encoding polynucleotide capable of expression in vivo to produce an effective adjuvant amount of interleukin-12.

Another embodiment provides a method for preventing, treating, or ameliorating infection by *Bordetella* in a host, comprising administering to the host a composition comprising at least one *Bordetella* antigen and an effective adjuvant amount of interleukin-12. Preferably, the antigen is a *Bordetella pertussis* antigen, or is lipopolysaccharide, pertussis toxin, filamentous hemagglutinin, or pertactin, or is adsorbed to alum, or is administered as an antigen-encoding polynucleotide under conditions in which the antigen is expressed in vivo. Preferably, the interleukin-12 may be administered as an interleukin-12-encoding polynucleotide under conditions in which the interleukin-12 is expressed in vivo.

In another embodiment, the invention provides a method for eliciting an immune response against *Bordetella* comprising administering a composition comprising at least one *Bordetella* antigen and an effective adjuvant amount of interleukin-12. Preferably, the antigen is a *Bordetella pertussis* antigen, or is lipopolysaccharide, pertussis toxin, filamentous hemagglutinin, or pertactin, or is absorbed to alum, or is administered as an antigen-encoding polynucleotide under conditions in which the antigen is expressed in vivo. Preferably, the interleukin-12 may be administered as an interleukin-12-encoding polynucleotide under conditions in which the interleukin-12 is expressed in vivo.

In a further embodiment, the present invention provides a method for eliciting an immune response against *Bordetella* comprising administering simultaneously a first composition comprising at least one *Bordetella* antigen and a second composition comprising an effective adjuvant amount of interleukin-12. Preferably, the antigen is a *Bordetella pertussis* antigen, or is lipopolysaccharide, pertussis toxin, filamentous hemagglutinin, or pertactin, or is adsorbed to alum, or is administered as an antigen-encoding polynucleotide under conditions in which the antigen is expressed in vivo. Preferably, the interleukin-12 may be administered as an interleukin-12-encoding polynucleotide under conditions in which the interleukin-12 is expressed in vivo.

Another embodiment of the present invention provides a method for stimulating clearance of *Bordetella* from a host comprising administering a composition comprising at least one *Bordetella* antigen and an effective adjuvant amount of interleukin-12. Preferably, the antigen is a *Bordetella pertussis* antigen, or is lipopolysaccharide, pertussis toxin, filamentous hemagglutinin, or pertactin, is adsorbed to alum, or is administered as an antigen-encoding polynucleotide under conditions in which the antigen is expressed in vivo. Preferably, the interleukin-12 may be administered as an interleukin-12-encoding polynucleotide under conditions in which the interleukin-12 is expressed in vivo.

A further embodiment provides a method for preparing an improved vaccine composition comprising combining an effective adjuvant amount of interleukin-12 with a vaccine composition comprising at least one *Bordetella* antigen. Preferably, the antigen is a *Bordetella pertussis* antigen, or is lipopolysaccharide, pertussis toxin, filamentous hemagglutinin, or pertactin, or is adsorbed to alum.

A method is also provided for preparing an improved vaccine composition comprising combining an effective adjuvant amount of interleukin-12 with a vaccine composition comprising at least one antigen-encoding polynucleotide capable of expression in vivo to provide at least one *Bordetella* antigen.

In another aspect of the invention, a method is provided for preparing an improved vaccine composition comprising combining a vaccine composition comprising at least one *Bordetella* antigen with an interleukin-12-encoding polynucleotide capable of expression in vivo to produce an effective adjuvant amount of interleukin-12.

Another embodiment of the invention provides, in a vaccine composition comprising at least one *Bordetella* antigen and an adjuvant, the improvement comprising employing as the adjuvant an effective adjuvant amount of interleukin-12. Preferably, the antigen is a *Bordetella pertussis* antigen, or is lipopolysaccharide, pertussis toxin, filamentous hemagglutinin, or pertactin, or is adsorbed to alum.

The invention also provides, in a vaccine composition comprising an adjuvant and at least one antigen-encoding polynucleotide capable of expression in vivo to produce at least one *Bordetella* antigen, the improvement comprising employing as the adjuvant an effective adjuvant amount of interleukin-12.

There is also provided as a further embodiment, in a vaccine composition comprising at least one *Bordetella* antigen and an adjuvant, the improvement comprising employing as the adjuvant an interleukin-12-encoding polynucleotide capable of expression in vivo to produce an effective adjuvant amount of interleukin-12.

Other aspects and advantages of the present invention will be apparent upon consideration of the following detailed description of preferred embodiments thereof.

DETAILED DESCRIPTION OF THE INVENTION

Figure 1:
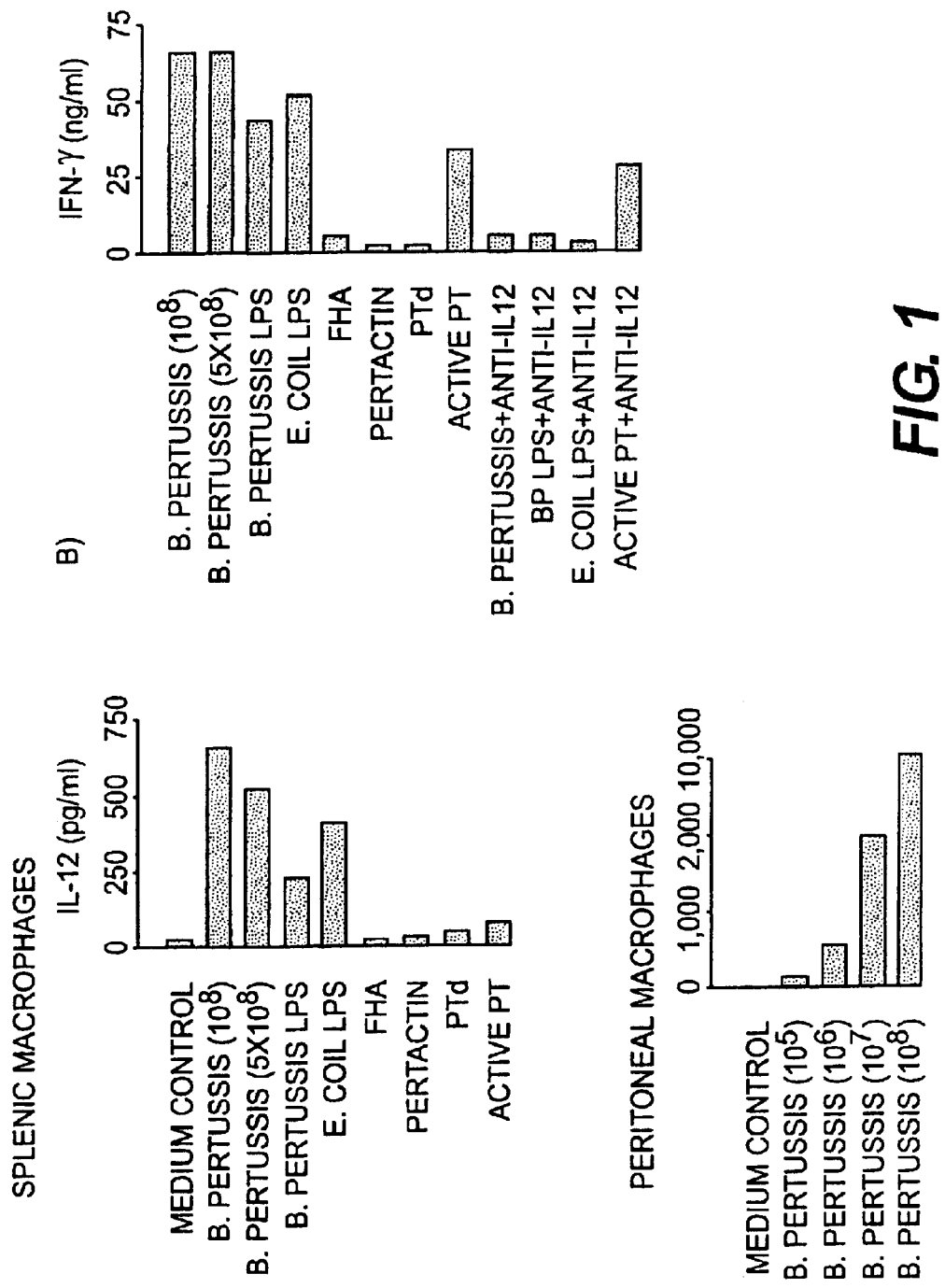
FIG. 1 is a bar graph showing IL-12 and IFN-γ production by macrophages stimulated with *Bordetella* antigens as described in Example 2.

The present inventors have for the first time demonstrated that the inclusion of IL-12 in an acellular vaccine against

*Bordetella* generated cell-mediated immune responses similar to those observed with whole-cell vaccines. A type 2 T helper cell (Th2) response normally induced following immunization of mice with an acellular *Bordetella* vaccine preparation can be switched to a Th1/Th0 response by incorporation of IL-12 into the vaccine formulation. The use of IL-12 as an adjuvant in an acellular pertussis vaccine significantly increased its protective efficacy; the rate of *B. pertussis* clearance from the lungs following respiratory challenge was equal to that observed with a potent whole-cell vaccine. These findings demonstrate a regulatory influence of IL-12 on the induction of *B. pertussis*-specific Th1 cells following infection or immunization and provides further evidence for the role of Th1 cells in protective immunity against *B. pertussis*. The present invention provides novel *Bordetella* vaccine compositions and methods of adjuvantation of *Bordetella* vaccines intended to provide a cell-mediated immune response against *Bordetella* by using IL-12 as an adjuvant.

As used herein, *Bordetella* includes *Bordetella pertussis*, *Bordetella parapertussis*, *Bordetella bronchiseptica*, and any other *Bordetella* strain or isolate that is sufficiently similar so that an immune response (including cell-mediated immunity and/or the generation of antibodies) raised against antigens present in one isolate will have an effect against at least some of the other strains or isolates.

A *Bordetella* antigen includes use of the whole *Bordetella* organism, a whole organism expressing *Bordetella* antigens, an antigenic portion of the *Bordetella* organism, recombinantly produced antigen or portions thereof or fusion proteins comprising antigens, and functional equivalents of *Bordetella* antigens. Antigenic portions of *Bordetella* organisms include lipopolysaccharide (LPS), filamentous hemagglutinin (FHA), pertactin, and pertussis toxin (PT). *Bordetella* LPS is preferably purified, for example, by gel filtration chromatography. Pertussis toxin may be active or untreated native pertussis toxin (aPT). Preferably, pertussis toxin may be inactivated pertussis toxin (iPT), such as pertussis toxin inactivated by heat treatment, or detoxified pertussis toxin (Ptd), such as pertussis toxin chemically detoxified by treatment with formaldehyde. *Bordetella* antigens may be adsorbed to alum. In addition, antigens of the present invention include polynucleotides which encode *Bordetella* antigens. Examples of such polynucleotides are those comprising the genes for *B. pertussis* FHA (Renauld-Mongenie, G. et al., 1996, *PNAS USA* 93: 7944–7949) and pertussis toxin (Steffen, P. et al., 1996, *EMBO J.* 15: 102–109). Other antigenic portions of *Bordetella* organisms that can be used in the compositions and methods of the present invention can be determined by those of ordinary skill in the art.

Interleukin-12 (IL-12), originally called natural killer cell stimulatory factor, is a heterodimeric cytokine described, for example, in M. Kobayashi et al., 1989, *J. Exp. Med.* 170: 827. IL-12 can be purified from natural sources, produced by chemical synthesis, or preferably produced by recombinant DNA techniques, for example by the expression and isolation of IL-12 protein in recombinant host cells as described in detail in International Patent Application WO90/05147, published May 17, 1990 (also European Patent Application No. 441,900), incorporated by reference herein. The DNA and amino acid sequences of the 30 kD and 40 kD subunits of the heterodimeric human IL-12 are provided in the above recited international application and in U.S. Pat. No. 5,571, 515, incorporated by reference herein. Research quantities of recombinant human and murine IL-12 are also available from Genetics, Institute, Inc., Cambridge, Mass.

As used herein, "interleukin-12" and "IL-12" refer to interleukin-12, its individual subunits, fragments thereof which exhibit IL-12 adjuvant activity, polynucleotides encoding IL-12, and functional equivalents of "interleukin-12" and "IL-12".

Functional equivalents of *Bordetella* antigens and IL-12 include modified *Bordetella* antigens and IL-12 protein such that the resulting *Bordetella* antigen or IL-12 product has the same antigenic or adjuvant activity, respectively, as described herein, and polynucleotide sequences that through the degeneracy of the genetic code encode *Bordetella* antigens or IL-12 polypeptides having the antigenic or IL-12 adjuvant activity, respectively, as described herein. For example, a functional equivalent of a *Bordetella* antigen or IL-12 can contain a "silent" codon amino acid substitution (for example, substitution of an acidic amino acid for another acidic amino acid, or substitution of a codon for a hydrophobic amino acid for another codon for a hydrophobic amino acid).

Fragments of *Bordetella* antigens and IL-12 are also encompassed by the present invention. Preferably, such fragments retain the desired antigenic or adjuvant activity or modify it to create a desired activity. Fragments of *Bordetella* antigens or IL-12 may be in linear form or they may be cyclized using known methods, for example, as described in H. U. Saragovi, et al., Bio/Technology 10, 773–778 (1992) and in R. S. McDowell, et al., J. Amer. Chem. Soc. 114, 9245–9253 (1992), both of which are incorporated herein by reference. The *Bordetella* antigens and IL-12 polypeptides provided herein also include antigens and IL-12 polypeptides characterized by amino acid sequences similar to those of purified antigens and IL-12 polypeptides but into which modifications are naturally provided or deliberately engineered. For example, modifications in the antigen or IL-12 polypeptide or antigen- or IL-12-encoding polynucleotide sequences can be made by those skilled in the art using known techniques. Modifications of interest in the *Bordetella* antigen or IL-12 polypeptide sequences may include the alteration, addition, insertion, deletion, mutation, substitution, replacement, or modification of a selected amino acid residue in the coding sequence. As one example, an additional amino acid may be added to the N-terminus of the antigen or of IL-12. Also, the amino acid sequence of the antigen or of IL-12 may be altered using random mutation techniques. It is also possible to attach to antigens or to IL-12 other moieties, including without limitation carbohydrates, lipids, or polyethylene glycol, or to remove or alter such moities. Techniques for such alterations, additions, insertions, deletions, mutations, substitutions, replacements, or modifications are well known to those skilled in the art (see, e.g., U.S. Pat. No. 4,518,584). Preferably such alteration, addition, insertion, deletion, mutation, substitution, replacement, or modification retains the desired activity of the *Bordetella* antigen or IL-12, or modifies it to create a desired activity.

The invention also encompasses allelic variants of disclosed *Bordetella* antigen- and IL-12encoding polynucleotides; that is, naturally-occurring alternative forms of isolated polynucleotides which also encode antigens or IL-12 polypeptides which are identical, homologous, or related to that encoded by the isolated polynucleotides.

Administration and Dosing

The IL-12 and the *Bordetella* antigen can be administered as a prophylactic vaccine to hosts, preferably to mammalian hosts, which are either infected or uninfected with *Bordetella*. The IL-12 and the antigen can also be administered as a therapeutic vaccine to infected hosts and can result in amelioration or elimination of the disease state due to infection by *Bordetella* organisms.

The amount of *Bordetella* antigen used in the compositions and methods of the present invention is an amount which produces an effective immunostimulatory response in the host. An effective adjuvant amount of IL-12 is an amount such that when administered it results in an enhanced immune response relative to the immune response when IL-12 is not administered. Such amounts of IL-12 will depend on the nature of the *Bordetella* antigen and the dosage amounts of the antigen. In addition, the amount of *Bordetella* antigen and IL-12 administered to the host will vary depending on a variety of other factors, including the antigen(s) employed, the size, age, body weight, general health, sex, and diet of the host, the time or duration of administration, and the particular qualities of the *Bordetella* infection being treated or vaccinated against. As one example, an effective adjuvanting amount of IL-12 polypeptide is desirably between about 0.1 μg to about 0.5 mg of IL-12 polypeptide per about 25 μg of antigen. The effective adjuvant amount for any particular vaccine or antigen will be readily defined by balancing the efficacy and toxicity of the IL-12 and antigen combination. Adjustment and manipulation of established dose ranges are well within the ability of those skilled in the art.

In the method of the present invention, an effective adjuvant amount of IL-12 is administered in combination with a *Bordetella* antigen, at a time closely related to immunization with the *Bordetella* antigen, so that an enhanced immune response is produced relative to an immunization in which IL-12 is not administered. Thus, the IL-12 can be administered prior to and preferably just prior to immunization, at the time of immunization (i.e. simultaneously), or after immunization (i.e. subsequently). If the IL-12 is administered before the vaccine composition, it is desirable to administer it about one or more days before the vaccine. In addition, the IL-12 can be administered prior to immunization with the *Bordetella* antigen, followed by subsequent injections of IL-12 after immunization with the antigen.

The IL-12 and the *Bordetella* antigen can be administered to a host in a variety of ways. The routes of administration include intradermal, transdermal (for example, by slow-release polymers), intramuscular, intraperitoneal, intravenous, subcutaneous, oral, aural, epidural, anal or vaginal (for example, by suppositories), and intranasal routes. Any other convenient route of administration can be used, for example, infusion or bolus injection, or absorption through epithelial or mucocutaneous linings. In addition, the IL-12 and the *Bordetella* antigen can be administered in combination with other components or biologically active agents, such as other known adjuvants, (for example, alum, MPL, QS21), pharmaceutically acceptable surfactants such as glycerides, excipients such as lactose, carriers diluents, and vehicles. If desired, certain sweetening, flavoring, and/ or coloring agents can also be added.

When used as an adjuvant for a vaccine composition containing a *Bordetella* antigen, IL-12 is desirably admixed as part of the vaccine composition itself, and administered by the same route as the vaccinal *Bordetella* antigen. Alternatively, the adjuvanting effect of IL-12 may be employed by administering IL-12 separately from the vaccine composition. When separately administered, the IL-12 is desirably in the presence of a suitable carrier, such as saline and optionally conventional pharmaceutical agents enabling gradual release of IL-12. The amount of IL-12 used in this mode of vaccination is similar to the ranges identified above when IL-12 is part of the vaccine composition.

Further, *Bordetella* antigens and/or IL-12 can be administered by in vivo expression in the host of polynucleotides encoding at least one *Bordetella* antigen and/or IL-12. Polynucleotides encoding IL-12 or a fragment thereof may be used as an adjuvant. The polynucleotides, preferably in the form of DNA, may be delivered to the vaccinated host for in vivo expression of *Bordetella* antigens and/or IL-12. So-called 'naked DNA' may be used to express *Bordetella* antigens and/or IL-12 in vivo in a host (Cohen, J., 1993, Science 259: 1691–1692; Fynan, E. et al., 1993, PNAS USA 90: 11478–11482; and Wolff, J. A. et al., 1991, Biotechniques 11:474–485 describe similar uses of 'naked DNA', all incorporated by reference herein.) For example, polynucleotides encoding IL-12 or fragments thereof may be incorporated, or transduced, into the *Bordetella* organism itself, if the whole *Bordetella* organism is to be employed as the vaccinal antigen. In another example, polynucleotides encoding *Bordetella* antigens may be incorporated or transduced into cells of another organism, such that the *Bordetella* antigens are expressed on the surface of the cells that may then be employed as the vaccinal antigen. Alternatively, polynucleotides encoding IL-12 or fragments thereof may be administered as part of the *Bordetella* vaccine composition or separately but contemporaneously with the vaccine antigen, for example, by injection.

Still other modes of delivering *Bordetella* antigens and/or IL-12 to the host in the form of polynucleotides encoding them are known to those of skill in the art and may be employed rather than administration of *Bordetella* antigens and/or IL-12 polypeptides, as desired. For example, polynucleotides encoding IL-12 may be administered as part of a vector or as a cassette containing the sequences encoding the *Bordetella* antigens and/or IL-12 operatively linked to a promoter sequence. (For example, see International Patent Application PCT WO94/01139, published Jan. 20, 1994 and incorporated by reference herein.) Briefly, the DNA encoding the *Bordetella* antigens and/or IL-12 protein or desired fragments thereof may be inserted into a nucleic acid cassette. This cassette may be engineered to contain, in addition to the antigen or IL-12 sequence to be expressed, other optional flanking sequences which enable its insertion into a vector. This cassette may then be inserted into an appropriate vector downstream of a promoter, an mRNA leader sequence, an initiation site, and other regulatory sequences capable of directing the replication and expression of that sequence in vivo. Additional regulatory sequences may be inserted downstream of the coding sequence to be expressed. This vector permits in vivo expression of the *Bordetella* antigens and/or IL-12 polypeptides within the host. When IL-12 polynucleotides are employed as the adjuvant, these polynucleotide sequences may be operatively linked to polynucleotide sequences which encode the *Bordetella* antigen(s).

IL-12 may be preferable to known adjuvants because of its enhancement of vaccine efficacy when cell-mediated immunity is required. IL-12 has an advantage over alum as a *Bordetella* vaccine adjuvant, as alum induces Th2 T helper cells rather than the Th1 cells induced by IL-12. Thus, alum-adjuvanted vaccines may be ineffectual for organisms such as *Bordetella* against which a Th1 response is most effective. Additionally, IL-12 is superior to bacterial adjuvants, such as BCG, which may induce in addition to IL-12 other agents or results which may be unanticipated or uncontrolled. More desirably, IL-12 as an adjuvant should not induce the uncontrolled production of other cytokines, as do bacterial adjuvants which induce IL-12 along with many other cutokines. Unlike bacterial adjuvants, IL-12 is human in origin and thus unlikely to produce any sensitization. Moreover, unlike other adjuvants such as IFN-γ or IL-2, IL-12 is relatively stable in vivo. Thus, it is anticipated that IL-12 will be a highly useful adjuvant for use in vaccines against *Bordetella*.

Patent and literature references cited herein are incorporated by reference as if fully set forth.

The following examples illustrate embodiments of the present invention, but are not intended to limit the scope of the disclosure.

EXAMPLE 1

Analysis of Cytokine Production

Mice. Female BALB/c mice were bred and maintained under the guidelines of the Irish Department of Health. All mice were 8 to 12 weeks old at the initiation of this and the following experiments.

Cytokine Production. T cell cytokine production was assessed using spleen cells from mice stimulated with *B. pertussis* antigens in vitro. Spleen cells ($2\times10^6$/ml) from immunized or naive control mice were cultured with antigens or with medium alone (background control), and supernatants were removed after 24 hours to determine IL-2 production and after 72 hours to determine the concentrations of IFN-γ, IL-4 and IL-5. IL-2 release were assessed by the ability of culture supernatants to support the proliferation of the IL-2-dependent CTLL-2 cell line. The concentrations of murine IL-4, IL-5, and IFN-γ were determined by specific immunoassays using commercially available antibodies (PharMingen, San Diego, Calif., USA) as previously described (B. P. Mahon, K. Katrak, A. Nomoto, A. J. Macadam, P. D. Minor, and K. H. G. Mills, 1995, *J. Exp. Med.* 181: 1285–1292) and incorporated herein by reference.

The concentration of IL-12 was determined by immunoassays and bioassays. In the immunoassays, commercially available anti-IL-12 monoclonal antibodies C17.8 (rat IgG2a) and C15.6 (rat IgG1) (Genzyme Diagnostics, Cambridge, Mass. (USA), which recognize the p40 subunit of murine IL-12 as a monomer, a homodimer, or as part of the p70 heterodimer, were used for capture and detection respectively. An alkaline phosphotase-conjugated mouse anti-rat IgG1 (PharMingen, San Diego, Calif., USA) was used to detect the second anti-IL-12 antibody. In the bioassays, biologically active IL-12 concentrations were assessed by the ability of test supernatants to stimulate the production of IFN-γ by naive spleen cell preparations. To ensure that the production of IFN-γ was due to the presence of IL-12, test samples were also assayed in the presence and absence of a specific anti-IL-12 neutralizing antibody (2.5 μg/ml of protein G-purified sheep anti-murine IL-12, Genetics Institute, Cambridge, Mass., USA) which can completely neutralize up to 5 ng/ml of IL-12. Cytokine concentrations were determined by comparing either the proliferation or the $OD_{492}$ for test samples with a standard curve for recombinant cytokines of known concentration.

EXAMPLE 2

Macrophages Secrete IL-12 in Response to *Bordetella* Antigens

This experiment tested the ability of killed whole *B. pertussis* and *B. pertussis* components to stimulate the production of IL-12 by murine macrophages.

Macrophages. Murine peritoneal macrophages were obtained from naive animals by plastic adherence of cells obtained by peritoneal lavage. Splenic macrophages were prepared by plastic adherence and alveolar macrophages were isolated by bronchoalveolar lavage as previously described (K. Redhead, A. Barnard, J. Watkins, and K. H. G. Mills, 1993, *Infect. Immun.* 61: 3190–3198). The murine macrophage cell line J774 was also used in studies of IL-12 production. Macrophages were infected with viable phase I *B. pertussis* at a bacteria to macrophage ratio of 5:1 for two hours before extensive washing. Extracellular bacteria were killed by treatment with polymyxin B sulphate (100 μg/ml) for 40 minutes followed by further washing. This treatment reduces the number of extracellular bacteria by 5.0 log CFU. Infected macrophages or macrophages stimulated with heat-inactivated bacteria or bacterial antigens were cultured at $2\times10^5$ cells/ml at 37° C. in a 5% $CO_2$ atmosphere. After 24 to 48 hours cell culture supernatants were removed and the production of IL-12 determined by bioassay or immunoassay, as described above in Example 1.

Antigens. The third British reference preparation for pertussis vaccine (88/522) was used as the whole-cell vaccine. Heat-killed *B. Pertussis* for use in proliferation assays was prepared by incubation of cells at 80° C. for 30 min. PT, FHA, and pertactin prepared from *B. Pertussis* Tohama strain, were kindly provided by Carine Capiau at SmithKline, Beecham, Rixensart, Belgium. Chemically detoxified PT (PTd) for immunization experiments was prepared by treatment with 0.2 to 0.5% formaldehyde for seven days followed by dialysis against PBS containing 0.01% formaldehyde. Inactivated PT (iPT) for use in proliferation assays was prepared by heating active PT at 80° C. for 30 minutes. (Active PT refers to untreated native PT throughout). LPS from *B. Pertussis* W28 (89/670) was obtained from The National Institute for Biological Standards and Control, Potters Bar, Herts, UK. LPS from *E. coli* (prepared by phenolic extraction and gel filtration chromatography) was purchased from Sigma Chemical Co., Poole, Dorset, UK.

FIG. 1 shows macrophage production of IL-12 in response to whole *B. pertussis* and components. IL-12 was tested by immunoassay (A) or by bioassay (B). Results from the immunoassay, which detects p40 and p70, are mean concentration in supernatants from triplicate cultures of splenic macrophages incubated with heat-killed *B. pertussis* ($1\times10^8$/ml and $5.0\times10^8$/ml), *B. pertussis* LPS (1 μg/ml), *E. coli* LPS (1 μg/ml), FHA (1 μg/ml), pertactin (1 μg/ml) active PT (1 μg/ml), detoxified PT (PTd, 1 μg/ml), or peritoneal macrophages incubated with increasing doses ($10^5$–$10^8$ CFU/ml) of heat-killed *B. pertussis*. The bioassay measured the production of IFN-γ produced by naive spleen cells incubated for 24 hours with supernatants from splenic macrophages (stimulated by incubation with antigen as described for the immunoassay) in the presence or absence of a polyclonal neutralizing anti-IL-12 antibody at 2.5 μg/ml. Levels of IFN-γ produced in the presence of anti-IL-12 antibody are only shown where positive responses were observed in the absence of the antibody and with one dose ($5.0\times10^8$/ml) of the killed bacteria. Results are means for triplicate assays, and are representative of four independent experiments. Standard deviations were less than 20% of the mean values.

Adherent cells from the spleens of naive mice stimulated with heat killed *B. pertussis* produced significant levels of IL-12, as described by an immunoassay specific for p40 and p70 (FIG. 1A). Moderate levels of IL-12 were also detected in supernatants from macrophages incubated with LPS derived from either *B. pertussis* or another Gram-negative bacterium *E. coli*. Tthese levels were enhanced when IFN-γ was added to the cultures (data not shown). In contrast, little or no IL-12 was produced by macrophages stimulated with FHA, PTd, or pertactin, the components of the acellular vaccine (FIG. 1A). Peritoneal macrophages also produced IL-12 in response to stimulation with heat-killed *B. pertussis* in a dose-dependent manner (FIG. 1A).

In order to demonstrate that the IL-12 produced was biologically active, we also tested IL-12 production using a bioassay, which measured the stimulation of IFN-γ by murine spleen cells in the presence or absence of a neutralizing polyclonal anti-IL-12 antibody. Supernatants from splenic macrophages that had been stimulated with killed bacteria or purified LPS induced naive spleen cells to produce high levels of IFN-γ, which was inhibited by the anti-IL-12 antibody (FIG. 1B). Although supernatants from spleen cells stimulated with active PT did stimulate the production of IFN-γ, this response could not be ablated by the addition of the anti-IL-12 antibody. Furthermore, IL-12 was not detected in supernatants of PT-stimulated macrophages using the immunoassay (FIG. 1A). Therefore, it is unlikely that active PT induces IL-12 from macrophages. Active PT is mitogenic for murine T cells and we have found that it promotes IFN-γ produced by purified splenic T cells in the presence of irradiated accessory cells (Ryan and Mill, unpublished observations). Therefore, the IFN-γ detected in the IL-12 bioassay using supernatants from macrophages stimulated with active PT is likely to result from direct stimulation of T cells in the spleen cell population by active PT carried over in the macrophage supernatants.

Live *B. pertussis* can be taken up by and survive within macrophages, so the production of IL-12 by macrophages following infection with *B. pertussis* was also examined. Table 1 shows the secretion of IL-12 by murine macrophages in response to infection with *B. pertussis*. Macrophages were infected with *B. pertussis* for two hours and extensively washed and treated with polymyxin B to kill extracellular bacteria prior to culture in the presence or absence of a neutralizing anti-IL-12 antibody. IL-12 production was assessed using bioassay which measured the production of IFN-γ by naive spleen cells incubated for 24 hours with supernatants from infected or control uninfected macrophages. Results are expressed as the mean (±SD) IFN-γ concentrations in the supernatants of triplicate cultures measured by immunoassay.

TABLE 1

| | | IFN-γ (pg/ml) | |
|---|---|---|---|
| Macrophage | Infected | No antibody | +anti-IL-12 |
| Alveolar | − | <50 | <50 |
| | + | 700 (41) | 100 (16) |
| Peritoneal | − | <50 | <50 |
| | + | 30,000 (2,245) | 75 (31) |
| J774 | − | <50 | <50 |
| | + | 900 (66) | <50 |

Although the levels of IL-12 are not as high as that observed following stimulation of peritoneal macrophages with killed bacteria (as in FIG. 1A), this may reflect the lower concentration of live bacteria used in this experiment. Higher levels of viable *B. pertussis* were employed in other experiments but resulted in cell death of the macrophage populations used in vitro. In separate experiments, supernatants of alveolar, peritoneal, J774, and splenic macrophages removed 24 and 48 hours after infection with *B. pertussis* were also found to contain IL-12 detected by the immunoassay (data not shown). Furthermore, peritoneal macrophages recovered from mice 24 hours after interperitoneal injection with live *B. pertussis* secreted significant levels of IL-12 (569 pg per ml of culture supernatant in one experiment) without further stimulation in vitro.

EXAMPLE 3

IL-12 Stimulates Immune Cell Proliferation in Response to *B. pertussis* Antigens We tested the ability of IL-12 to modulate immune response to *B. pertussis* antigens in vivo by immunization of mice with FHA and PTd in the presence or absence of alum. Spleen cells from immunized or control mice were tested for in vitro proliferation against heat-killed *B. pertussis* ($10^6$/ml), heat-inactivated PT (1.0 μg/ml), FHA (1.0 μg/ml), and pertactin (1.0 μg/ml) as previously described (K. H. G. Mills, A. Bernard, J. Watkins, and K. Redhead, 1993, *Infect. Immun.* 61: 399–410) and incorporated herein by reference. Results were calculated as mean counts per minute (CPM) of [$^3$H] thymidine incorporation for triplicate cultures for groups of four to six mice. Stimulation indices were calculated by dividing the proliferative response to the antigens by the response of control cultures, where cells were stimulated with medium alone.

Recombinant murine IL-12 was kindly provided by Stanley Wolf, Genetics Institute, Inc., Cambridge, Mass., USA. Spleen cells from mice immunized with soluble or alum-adsorbed FHA and PTd, with or without IL-12 (0.5 μg), were stimulated in vitro with iPT (1.0 μg/ml), FHA (5.0 μg/ml), or medium alone. Proliferative responses were measured by $^3$H thymidine incorporation after four days and are expressed as counts per minute (CPM) and stimulation indices (SI). The levels of IFN-γ and IL-5 were tested in supernatants after 72 hours of culture. Results are mean (±SD) responses for triplicate cultures for four mice in each group. —, below the level of detection. * and **, P<0.01 and P<0.001, respectively, compared to the corresponding value for mice immunized in the absence of IL-12, determined by Student's t test.

TABLE 2

| Immunization | In vitro Stimulation | Proliferation | | IFN-γ | IL-5 |
|---|---|---|---|---|---|
| | | CPM | SL | (ng/ml) | (pg/ml) |
| FHA + PTd | Medium | 118 ± 40 | — | — | — |
| | FHA | 129 ± 53 | 1.1 ± 0.4 | 1.8 ± 0.5 | — |
| | iPT | 98 ± 34 | 0.8 ± 0.4 | 2.2 ± 0.8 | — |
| FHA + PTd + IL-12 | Medium | 1,347 ± 191 | — | — | — |
| | FHA | 8,412 ± 1491 | 6.2' ± 0.9 | 12.3" ± 1.0 | — |
| | iPT | 8,985 ± 3793 | 6.7' ± 1.6 | 11.0" ± 0.9 | — |
| FHA + PTd + alum | Medium | 2,380 ± 168 | — | — | — |
| | FHA | 13,264 ± 3,010 | 5.6 ± 2.8 | 5.7 ± 0.6 | 410 ± 70 |
| | iPT | 6,389 ± 2,123 | 2.7 ± 0.8 | 12.1 ± 1.3 | 430 ± 60 |
| FHA + PTd + alum + IL-12 | Medium | 1,546 ± 823 | — | — | — |
| | FHA | 17,953 ± 4,436 | 11.6 ± 3.4 | 7.4 ± 3.0 | 140' ± 30 |
| | iPT | 7,706 ± 4,128 | 5.0 ± 3.0 | 16.3 ± 2.0 | 110' ± 20 |

Table 2 shows that co-injection with IL-12 augments cellular immune responses to *B. pertussis* antigens. Two weeks after immunization with FHA and PTd in solution, the in vitro proliferative responses of spleen cells against the specific antigens were similar to that observed against medium alone (Table 2). In contrast, immunization with FHA and PTd in the presence of IL-12 resulted in enhanced proliferative responses to FHA, iPT (Table 2) and killed whole bacteria (data not shown). The addition of IL-12 to the alum-adsorbed antigens also augmented the B. pertussis-specific proliferative responses, although this did not reach a level of statistical significance (Table 2).

Co-injection of soluble antigens and IL-12 enhanced the level of IFN-γ secreted in vitro by antigen stimulated spleen cells; IL-5, a Th2 type cytokine, was not detected from spleen cells from these animals (Table 2). In contrast, spleen cells from mice immunized with FHA and PTd in the presence of alum secreted high levels of IL-5 and moderate levels of IFN-γ, confirming the known effect of alum to favor the induction of Th2 type responses in mice. However, co-injection of IL-12 with FHA and PTd adsorbed to alum resulted in a reduction in IL-5 production, but not a significant increase in the level of IFN-γ secreted, when compared with spleen cells from animals which had received antigens formulated with alum in the absence of IL-12 (Table 2).

EXAMPLE 4

Figure 2:
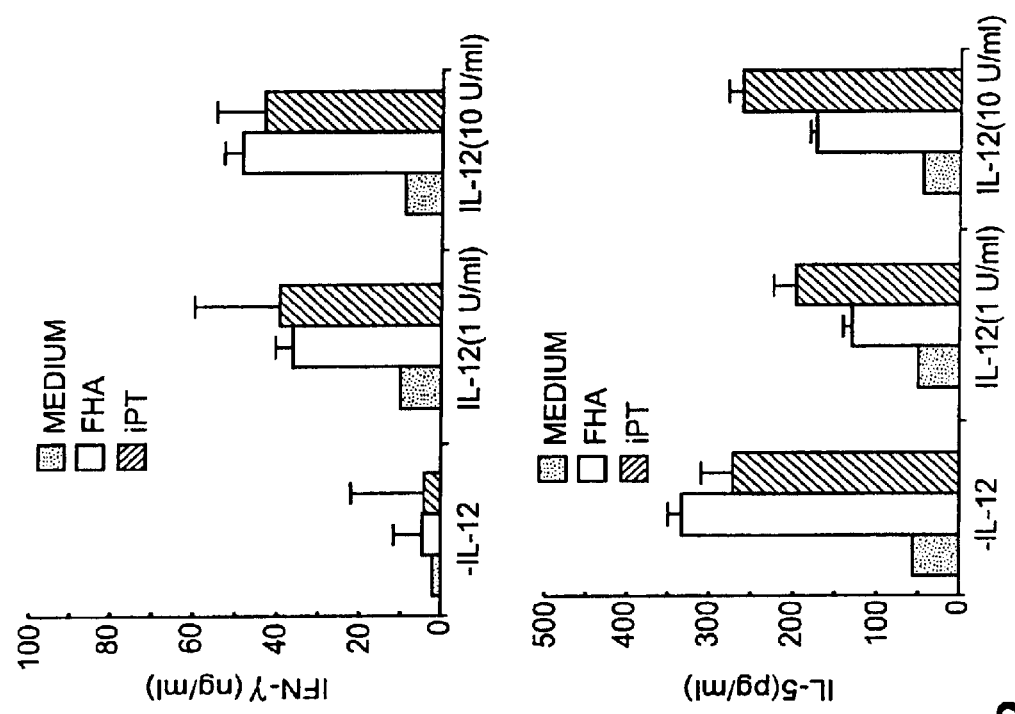
FIG. 2 is a bar graph showing IL-5 and IFN-γ production by spleen cells from mice immunized with *Bordetella* antigens, then stimulated in vivo with *Bordetella* antigens in combination with IL-12, as described in Example 4.
Figure 3:
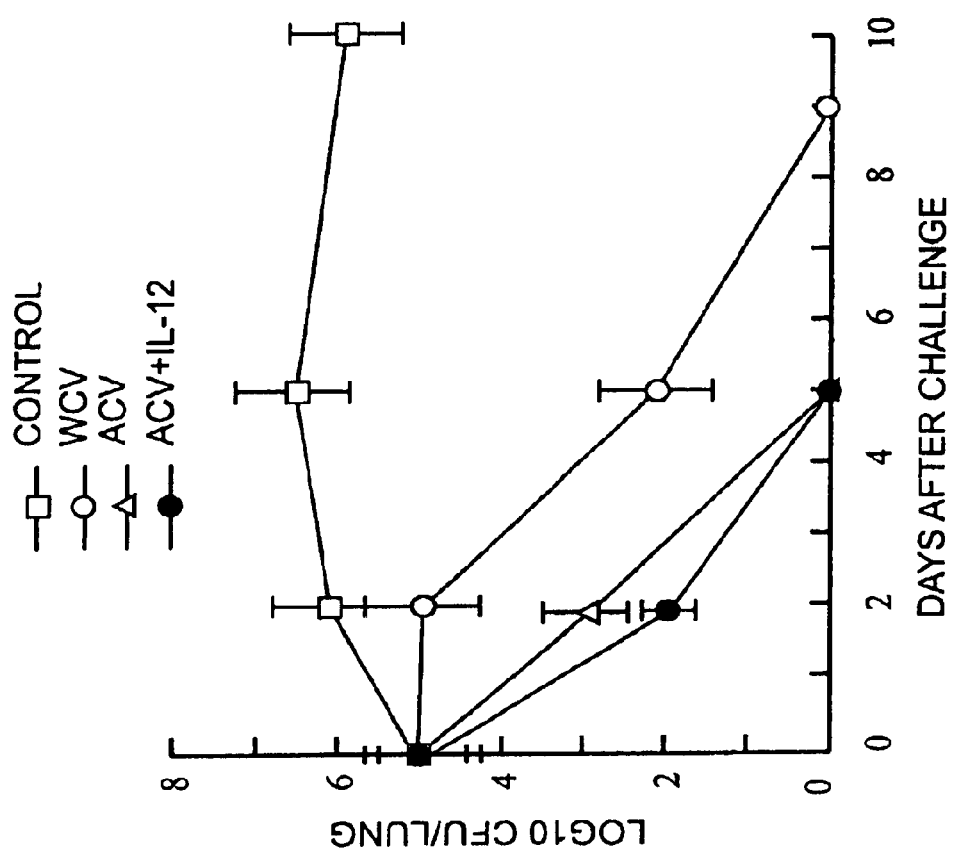
FIG. 3 is a graph showing counts of viable *B. pertussis* cells in the lungs of mice immunized with *B. pertussis* whole-cell or acellular vaccines with or without IL-12, then challenged with live *B. pertussis,* as described in Example 5.

IL-12 Stimulates IFN-γ Production by Immune Cells from Mice Immunized with Bordetella Antigens Addition of IL-12 in vitro augments IFN-γ production by spleen cells from mice primed for a Th2 response, as shown in FIG. 2. Mice were immunized with FHA and PTd in alum and spleen cells were stimulated in vitro with FHA, inactivated PT (iPT, 1.0 µg/ml), or medium alone in the presence of 0, 0.2, and 2.0 ng/ml of recombinant murine IL-12. The levels of IFN-γ and IL-5 were tested in spleen cell supernatants after 72 hours. Results are expressed as the mean (±SE) cytokine concentration for stimulated spleen cells from four mice per group tested in triplicate.

Immunization of mice with FHA and PTd adsorbed to alum generated a potent Th2 response; ex vivo spleen cells produced high levels of IL-5 and low levels of IFN-γ following specific antigen stimulation in vitro (FIG. 2). However, the addition of 0.2 or 2.0 ng per ml of recombinant murine IL-12 to the spleen cells during antigen stimulation in culture resulted in significantly increased concentrations of IFN-γ and marginally reduced levels of IL-5 (FIG. 2), demonstrating that IL-12 can modulate the pattern of in vitro cytokine secretion by in vivo printed T cells.

EXAMPLE 5

Adjuvant Effect of IL-12 on Immunization with an Acellular Pertussis Vaccine

Since we had previously demonstrated that a high procedure whole-cell vaccine induces a Th1 response, we decided to compare the immune responses and protection induced with a whole-cell vaccine with an acellular vaccine administered in the presence or absence of IL-12. In these studies of the adjuvant effect of IL-12 on immunization with a Bordetella pertussis acellular vaccine, groups of 20 mice received two intraperitoneal (i.p.) immunizations four weeks apart with ⅕ a human dose (0.8 IU) of the whole-cell vaccine (88/522), or with an acellular vaccine comprising 5 µg each of FHA, pretactin, and PTd with or without recombinant murine IL-12 (0.5 µg/mouse). Control mice received PBS medium alone. Two weeks after the second immunization, mice were either sacrificed to assess immune response or challenged with B. pertussis.

Aerosol Infection. Respiratory infection of mice was initiated by aerosol challenge using the method originally described by Sato et al. (1980, *Infect. Immun.* 29: 261–266), with the following modification. *B. pertussis W*28 Phase I was grown under agitation conditions at 36° C. in Stainer-Scholte liquid medium. Bacteria from a 48-hour culture were resuspended at a concentration of approximately $2\times10^{10}$ colony forming units (CFU) per ml in physiological saline containing 1% casein. The challenge inoculum was administered as an aerosol over a period of 12 minutes using a nebulizer directed into an aerosol chamber containing groups of 20–24 mice. Four mice from each experimental group were sacrificed at 2 hours and at 2, 5, and 9 days after aerosol challenge to assess the number of viable *B. pertussis* in the lungs.

Enumeration of Viable Bacteria in the Lungs. Lungs were removed aseptically and homogenized in 1 ml of sterile physiological saline with 1% casein on ice. 100 μl of undiluted homogenate or of serially diluted homogenate from individual lungs were spotted in triplicate onto each of three Bordet-Gengou agar plates and the number of CFU was estimated after 5 days of incubation. Results are reported as the mean viable *B. pertussis* for individual lungs from four mice. The limit of detection was approximately $\log_{10}$ 0.5 CFU per lung.

BALB/c mice were immunized at 0 and 4 weeks with a whole cell vaccine (WCV), an acellular vaccine (ACV; 5 μg each of soluble PTd, FHA, and pertactin) with or without 0.5 μg IL-12, or PBS alone (Control). Mice were challenged by aerosol inoculation with *B. pertussis* two weeks after the second immunization. The course of respiratory infection was followed by performing viable counts at intervals after challenge. Results are mean (±SE) CFU counts performed on individual lungs in triplicate for four mice per group at each time point.

IL-12 as an adjuvant enhances the protective efficacy of an acellular pertussis vaccine, as shown in FIG. 3. The level of bacteria in the control mice were still high nine days after challenging (FIG. 3). The time course of respiratory infection in mice immunized with the whole cell vaccine was very short with complete clearance by day 5. Bacterial clearance in mice immunized with the acellular vaccine was slower, complete clearance did not occur until day 9 post challenge. However, the addition of IL-12 to the acellular vaccine formulation significantly enhanced its protective efficacy. Bacterial clearance was complete by day 5 and the bacterial burden on day 2 was lower than that observed in mice immunized with the whole cell vaccine (FIG. 3).

In order to confirm our earlier suggestions on the protective role of Th1 cells, and to establish that the superior protective efficacy observed with the acellular vaccine injected with IL-12 was due to enhanced cell mediated immunity, we also tested the immune response of the immunized mice on the day of challenge. IL-12 switches the immune response of spleen cells stimulated with an acellular pertussis vaccine from a Th2 response to a Th1/Th0 response, as shown in FIG. 4. Mice were immunized as described above for FIG. 3 with a whole cell vaccine (WCV), an acellular vaccine (ACV; 5 μg each of soluble PTd, FHA, and pertactin) with or without 0.5 μg IL-12, or PBS alone (Control). The secretion of IL-2, IFN-γ, and IL-5 was tested following stimulation of spleen cells from immunized mice with iPT (0.2–1.0 μg/ml). FHA (0.2–5.0 μg/ml), and pertactin (0.2–5.0 µg/ml) Results are expressed as the mean (±SE) cytokine concentration to optimum concentration of antigen for spleen cells from four mice per group tested in triplicate.

Figure 4:
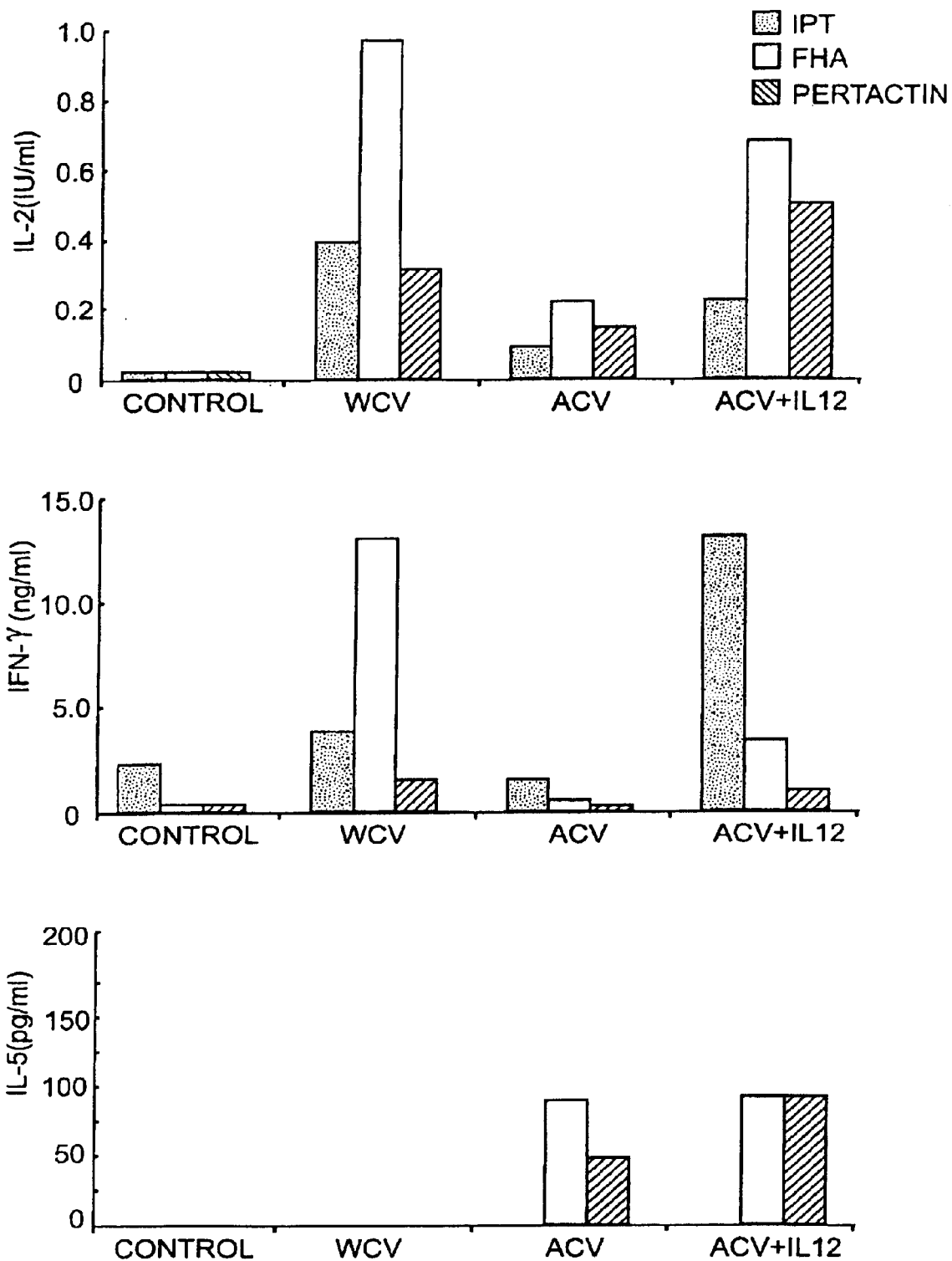
FIG. 4 is a bar graph showing the production of IL-2, IFN-γ, and IL-5 by spleen cells from mice immunized with *B. pertussis* whole-cell or acellular vaccines with or without IL-12, then stimulated in vitro with *Bordetella* antigens, as described in Example 5.

Proliferative responses were detected against whole killed *B. pertussis*, FHA, inactivated PT, and pertactin in spleen cells from mice immunized with the acellular vaccine, but these were significantly enhanced in the presence of IL-12 and approached the levels observed with the whole-cell vaccine (ref 20 and data not shown). An examination of the cytokine profiles produced by spleen cells stimulated with specific antigen in vitro revealed that spleen cells derived from mice immunized with the whole-cell vaccine secreted IL-2 and IFN-γ but no detectable IL-5 (FIG. 4). In contrast, spleen cells from mice which received the acellular vaccine in the absence of IL-12 secreted low levels of IL-2 and IFN-γ and low but detectable levels of IL-5. However, spleen cells from mice immunized with the acellular vaccine in the presence of IL-12 secreted significant levels of IL-2 and IFN-γ. Interestingly, IL-12 appeared to have differential effects on T cells of different antigen specificity, potentiating IL-2 production by T cells specific for FHA and pertactin and IFN-γ production by PT-specific T cells. Overall, the immune response induced with the acellular vaccine incorporating IL-12 as an adjuvant is best described as a mixed Th1/Th2 or Th0 profile.

These significant new findings are that tissue macrophages, including those recovered from the lung, spleen, or peritoneal cavity of naive mice, produce IL-12 following exposure to live or killed *B. pertussis* and that the addition of IL-12 as an adjuvant to a pertussis acellular vaccine enhances its protective efficacy by promoting type 1 T cell cytokine production. We have demonstrated that immunization of mice with a pertussis acellular vaccine comprising PTd. FHA, and pertactin adsorbed to alum, generated a Th2 response in mice and was associated with delayed bacterial clearance following respiratory challenge.

What is claimed is:

1. An acellular composition for enhancing cell-mediated immunity in a host, the composition comprising a *Bordetella pertussis* antigen consisting of one or more of isolated lipopolysaccharide and isolated filamentous hemagglutinin, and an amount of interleukin-12 sufficient to enhance cell-mediated immunity in a host.

2. The composition of claim 1 wherein the antigen is lipopolysaccharide.

3. The composition of claim 1 wherein the antigen is adsorbed to alum.

4. An acellular composition for enhancing cell-mediated immunity in a host, the composition comprising (a) an amount of interleukin -12 sufficient to enhance cell-mediated immunity in a host, (b) and at least one isolated polynucleotide encoding a *Bordetella pertussis* filamentous hemagglutinin, wherein the polynucleotide, when introduced into a host, is expressed to produce the *Bordetella pertussis* antigen.

5. An acellular composition for enhancing cell-mediated immunity in a host, the composition comprising a *Bordetella pertussis* antigen of one or more of isolated lipopolysaccharide and isolated filamentous hemagglutinin, and an interleukin-12-encoding polynucleotide, wherein the polynucleotide, when introduced into a host, is expressed to produce interleukin-12 in an amount sufficient to enhance cell-mediated immunity in said host.

6. A method for preventing, treating, or ameliorating infection by *Bordetella pertussis* in a host, comprising administering to the host the acellular composition of claim 1.

7. A method for preventing, treating, or ameliorating infection by *Bordetella pertussis* in a host, comprising administering to the host an acellular composition comprising a *Bordetella pertussis* antigen consisting of one or more of isolated lipopolysaccharide and isolated filamentous hemagglutinin, and an amount of interleukin-12 sufficient to enhance cell-mediated immunity in said host.

8. The method of claim 7 wherein the antigen is lipopolysaccharide.

9. The method of claim 7 wherein the antigen is adsorbed to alum.

10. The method of claim 7 wherein the antigen is administered as an antigen-encoding polynucleotide, wherein the polynucleotide when introduced into a host is expressed to produce a *Bordetella pertussis* filamentous hemagglutinin.

11. The method of claim 7 wherein the interleukin-12 is administered as an interleukin-12-encoding polynucleotide, wherein the polynucleotide when introduced into a host, is expressed to produce interleukin-12.

12. A method for eliciting a cell-mediated immune response against *Bordetella* in a host, comprising administering an acellular composition comprising a *Bordetella pertussis* antigen consisting of one or more of isolated lipopolysaccharide and isolated filamentous hemagglutinin, and an amount of interleukin-12 sufficient to enhance cell-mediated immunity in said host.

13. The method of claim 12 wherein the antigen is lipopolysaccharide.

14. The method of claim 12 wherein the antigen is adsorbed to alum.

15. The method of claim 12 wherein the antigen is administered as an antigen-encoding polynucleotide, wherein the polynucleotide, when introduced into a host, is expressed to produce a *Bordetella pertussis* antigen consisting of filamentous hemagglutinin.

16. The method of claim 12 wherein the interleukin-12 is administered as an interleukin-12-encoding polynucleotide, wherein the polynucleotide, when introduced into a host, is expressed to produce interleukin-12.

17. A method for eliciting a cell-mediated immune response against *Bordetella* in a host, the method comprising administering simultaneously a first acellular composition comprising a *Bordetella pertussis* antigen consisting of one or more of isolated lipopolysaccharide and isolated filamentous hemagglutinin, and a second composition comprising an amount of interleukin-12 sufficient to enhance cell-mediated immunity in said host.

18. The method of claim 17 wherein the antigen is lipopolysaccharide.

19. The method of claim 17 wherein the antigen is adsorbed to alum.

20. The method of claim 17 wherein the antigen is administered as an antigen-encoding polynucleotide, wherein the polynucleotide, when introduced into a host, is expressed to produce a *Bordetella pertussis* antigen consisting of filamentous hemagglutinin.

21. The method of claim 17 wherein the interleukin-12 is administered as an interleukin-12-encoding polynucleotide, wherein the polynucleotide, when introduced into a host, is expressed to produce interleukin-12.

22. A method for stimulating clearance of *Bordetella* from a host comprising administering an acellular composition comprising at least one purified *Bordetella pertussis* antigen consisting of one or more of isolated lipopolysaccharide and isolated filamentous hemagglutinin and an amount of interleukin-12 sufficient to enhance cell-mediated immunity in said host.

23. The method of claim 22 wherein the antigen is lipopolysaccharide.

24. The method of claim 22 wherein the antigen is adsorbed to alum.

25. The method of claim 22 wherein the antigen is administered as an antigen-encoding polynucleotide, wherein the polynucleotide, when introduced into a host, is expressed to produce a *Bordetella pertussis* antigen consisting of filamentous hemagglutinin.

26. The method of claim 22 wherein the interleukin-12 is administered as an interleukin-12-encoding polynucleotide, wherein the polynucleotide, when introduced into a host, is expressed to produce interleukin-12.

27. A method for preparing an improved vaccine composition for enhancing cell-mediated immunity, the method comprising combining an amount of interleukin-12 sufficient to enhance cell-mediated immunity in a host with an acellular vaccine composition comprising a *Bordetella pertussis* antigen consisting of one or more isolated lipopolysaccharide and isolated filamentous hemagglutinin.

28. The method of claim 27 wherein the antigen is lipopolysaccharide.

29. The method of claim 27 wherein the antigen is adsorbed to alum.

30. A method for preparing an improved vaccine composition for enhancing cell-mediated immunity, the method comprising combining an (a) amount of interleukin-12 sufficient to enhance cell-mediated immunity in a host wiht (b) an acellular vaccine composition comprising at least one isolated polynucleotide encoding a *Bordetella pertussis* antigen consisting of filamentous hemagglutinin, wherein the polynucleotide, when introduced into a host, is expressed to produce the *Bordetella pertussis* antigen.

31. A method for preparing an improved vaccine composition comprising combining an acellular vaccine composition comprising a *Bordetella pertussis* antigen consisting of one or more of isolated lipopolysaccharide and isolated filamentous hemagglutinin with an interleukin-12 encoding polynucleotide, wherein the polynucleotide, when introduced into a host, is expressed to produce interleukin-12 in an amount sufficient to enhance cell-mediated immunity in said host.

32. In a vaccine composition comprising a *Bordetella* antigen and an adjuvant, the improvement comprising employing as an adjuvant an amount of interleukin-12 sufficient to enhance cell-mediated immunity in a host and employing a *Bordetella pertussis* antigen consisting of one or more of isolated lipopolysaccharide and isolated filamentous hemagglutinin.

33. The method of claim 31 wherein the antigen is lipopolysaccharide.

34. The method of claim 31, wherein the antigen is adsorbed to alum.

35. In a vaccine composition comprising an adjuvant and at least one antigen-encoding polynucleotide, wherein the polynucleotide, when introduced into a host, is expressed to produce at least one antigen, the improvement comprising employing as the adjuvant an amount of interleukin-12 sufficient to enhance cell-mediated immunity in a host and employing a polynucleotide that is expressed to produce a *Bordetella pertussis* antigen consisting of isolated filamentous hemagglutinin.

36. In a vaccine composition comprising at least one *Bordetella* antigen and an adjuvant, the improvement comprising employing as the adjuvant an interleukin-12-encoding polynucleotide, wherein the polynucleotide, when introduced into a host, is expressed to produce interleukin-12 in an amount sufficient to enhance cell-mediated immunity in said host and employing a purified *Bordetella pertussis* antigen consisting of one or more isolated lipopolysaccharide and isolated filamentous hemagglutinin.

37. The composition of claim 1 wherein the antigen is filamentous hemagglutinin.

38. The method of claim 7 wherein the antigen is filamentous hemagglutinin.

39. The method of claim 12 wherein the antigen is filamentous hemagglutinin.

40. The method of claim 17 wherein the antigen is filamentous hemagglutinin.

41. The method of claim 22 wherein the antigen is filamentous hemagglutinin.

42. The method of claim 27 wherein the antigen is filamentous hemagglutinin.

43. The method of claim 31 wherein the antigen is filamentous hemagglutinin.

* * * * *